(12) United States Patent
Fry et al.

(10) Patent No.: US 7,057,730 B2
(45) Date of Patent: Jun. 6, 2006

(54) APPARATUS AND METHOD FOR DIRECT MEASUREMENT OF ABSORPTION AND SCATTERING COEFFICIENTS IN SITU

(75) Inventors: Edward S. Fry, College Station, TX (US); George W. Kattawar, College Sation, TX (US); Deric J. Gray, Nacogdoches, TX (US); Xianzhen Zhao, College Station, TX (US); Zheng Lu, College Station, TX (US)

(73) Assignee: The Texas A&M University System, College Station, TX (US)

( * ) Notice: Subject to any disclaimer, the term of this patent is extended or adjusted under 35 U.S.C. 154(b) by 360 days.

(21) Appl. No.: 10/715,336

(22) Filed: Nov. 17, 2003

(65) Prior Publication Data
US 2004/0141179 A1    Jul. 22, 2004

Related U.S. Application Data

(60) Provisional application No. 60/426,733, filed on Nov. 15, 2002.

(51) Int. Cl.
G01N 21/00 (2006.01)

(52) U.S. Cl. ....................................... 356/432
(58) Field of Classification Search ...................... None
See application file for complete search history.

(56) References Cited

U.S. PATENT DOCUMENTS 5,424,840 A  6/1995 Moore et al. ............... 356/410
5,712,710 A  1/1998 Karakus et al. ............. 356/436
6,580,091 B1 * 6/2003 Eriguchi et al. ............. 257/48
6,664,071 B1 * 12/2003 Windhab et al. ........... 435/7.94

FOREIGN PATENT DOCUMENTS

DE    197 51 403 A1    5/1999

OTHER PUBLICATIONS

PCT International Search Report dated May 13, 2004 for PCT/US03/36668, dated Nov. 17, 2003.
Friedman, et al., "Absorption Coefficient Instrument for Turbid Natural Waters," *Applied Optics*, vol. 19, No. 10, pp. 1688-1693, May 15, 1980.
Leathers, et al., "Analysis of a Point-Source Integrating-Cavity Absorption Meter," *Applied Optics*, vol. 39, No. 33, pp. 6118-6127, Nov. 20, 2000.

* cited by examiner

*Primary Examiner*—Gregory J. Toatley, Jr.
*Assistant Examiner*—Ali Allawi
(74) *Attorney, Agent, or Firm*—Baker Botts L.L.P.

(57) ABSTRACT

An apparatus for measuring an absorption coefficient includes a first diffusive material, a second diffusive material inside the first diffusive material separated from the first diffusive material by a cavity, and a transparent material proximate to an inner surface of the second diffusive material that holds an absorptive material. First and second light detectors measure light intensities in the first and second diffusive materials respectively. An absorption coefficient for the absorptive material may be determined based on the first and second light intensities measured when the cavity is illuminated by a light source.

31 Claims, 2 Drawing Sheets

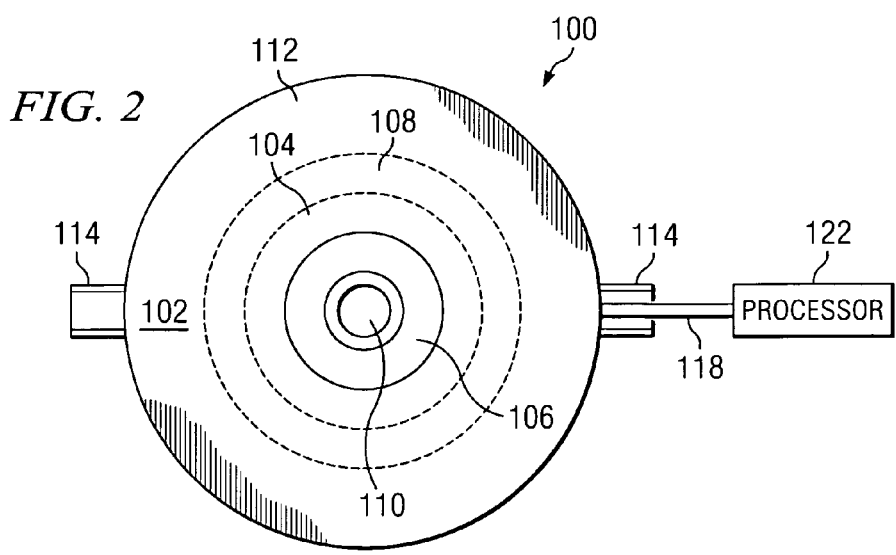
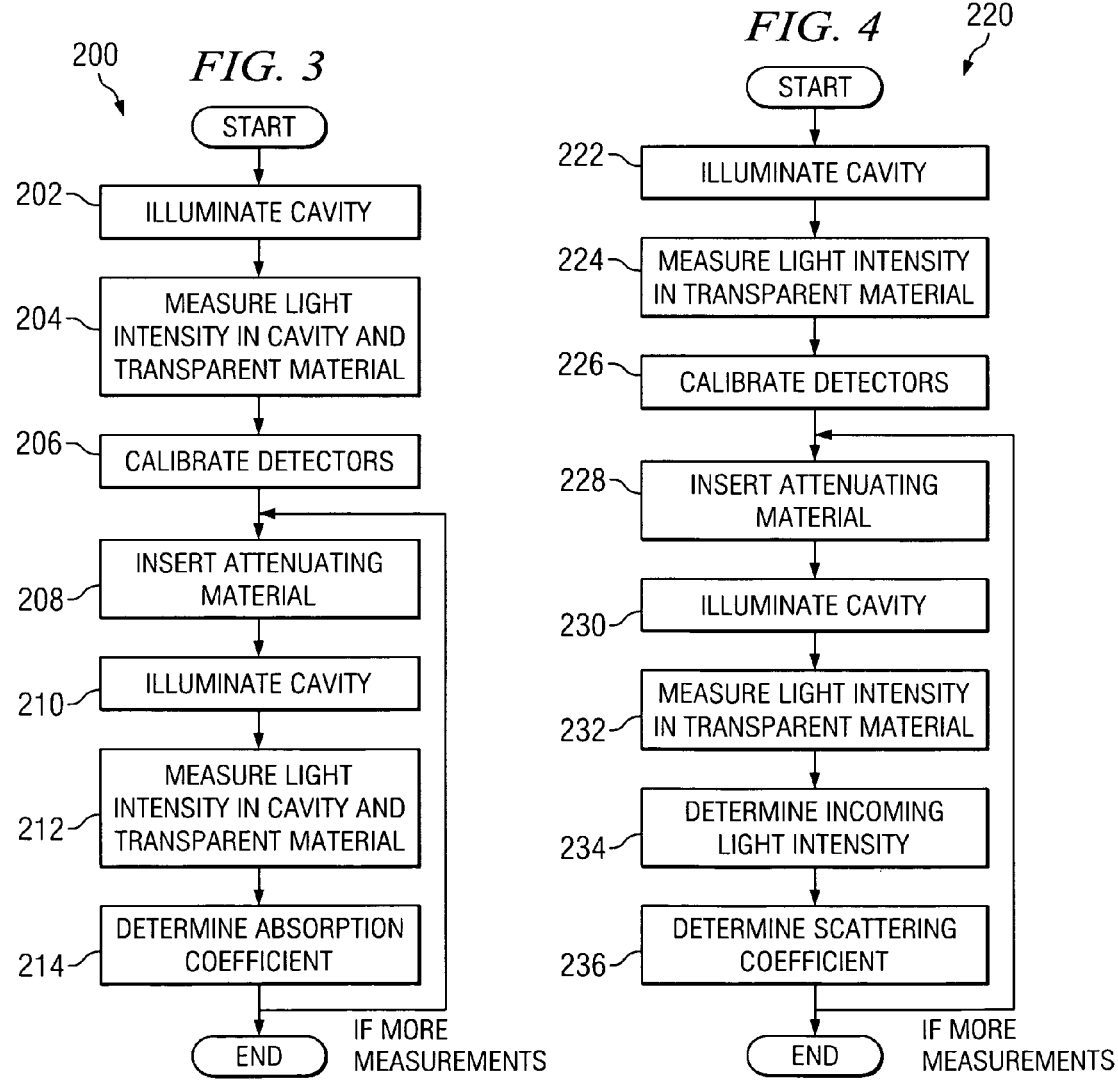

US 7,057,730 B2

APPARATUS AND METHOD FOR DIRECT MEASUREMENT OF ABSORPTION AND SCATTERING COEFFICIENTS IN SITU

RELATED APPLICATIONS

This application claims the benefit under 35 U.S.C. section 119(e) of the priority of U.S. Provisional Application No. 60/426,733, filed Nov. 15, 2002, entitled "An In Situ Device, System and Method to Directly Measure Both the Absorption and Scattering Coefficients of Natural Waters."

TECHNICAL FIELD OF THE INVENTION

This invention relates in general to measuring absorption and scattering coefficients of materials, and more particularly to an apparatus and method for direct measurement of absorption and scattering coefficients in situ.

BACKGROUND OF THE INVENTION

It is often useful in analyzing materials to characterize the response of those materials to incoming light (electromagnetic radiation). Two known coefficients for measuring these properties are absorption and scattering coefficients. An absorption coefficient can be expressed as the property of a medium that describes the amount of absorption of radiation per unit path length within the medium. It can be interpreted as the inverse of the mean free path that a photon will travel before being absorbed (if the absorption coefficient does not vary along the path). The unit quantity for an absorption coefficient is inverse length. A scattering coefficient can be expressed as the property of a medium that describes the amount of scattering of radiation per unit path length for propagation in the medium. It can be interpreted as the inverse of the mean free path that a photon will travel before undergoing scattering (if the scattering coefficient does not vary along the path). The unit quantity for a scattering coefficient is inverse length. Along with the scattering coefficient, an absorption coefficient describes the change in radiation intensity per unit length along the path through the medium.

Existing approaches to obtaining a scattering coefficient, b, involve measuring a volume scattering function using an array of detectors placed at various angles around the scattering material. The scattering coefficient is then calculated by integrating the volume scattering function over all angles. Traditionally, the scattering coefficient is obtained by measuring the extinction coefficient, c, using the relation b=c−a, where a is the absorption coefficient. The extinction coefficient, c, is a constant that predicts the attenuation or dissipation of light at a certain wavelength. In pure water, light is highly absorbed in the infrared region of the light spectrum and poorly absorbed in the blue region. Extinction coefficients are influenced by water absorption, suspended organic and inorganic particles, and dissolved compounds. Thus, the visible color in a water sample is the light that is refracted, reflected or re-emitted by substances in water because it has not been absorbed to produce heat or chemical reactions. The absorption coefficient, a, is also measured and, using the relation b=c−a, the scattering coefficient, b, can be calculated. However, sometimes this method can yield unphysical values of the scattering coefficient, b.

As for the measurement of the absorption coefficients of light in water, U.S. Pat. No. 5,424,840 to C. C. Moore and J. R. V. Zaneveld describes a method that can measure the absorption of chlorophyll for a single wavelength, and which was adapted by C. C. Moore and J. R. V. Zaneveld to be usable for nine discrete wavelengths. The major disadvantages of this device are: (1) it cannot measure the scattering coefficient directly; and (2) the accuracy of the measured absorption coefficient depends on how the scattered light is collected and accounted for. Therefore, there remains a need for a device, system and method for measuring more directly the above coefficients with relative accuracy.

SUMMARY OF THE INVENTION

In accordance with one embodiment of the present invention, an apparatus for measuring an absorption coefficient includes a first diffusive material, a second diffusive material inside the first diffusive material separated from the first diffusive material by a cavity, and a transparent material proximate to an inner surface of the second diffusive material that holds an absorptive material. First and second light detectors measure light intensities in the first and second diffusive materials respectively. An absorption coefficient for the absorptive material may be determined based on the first and second light intensities measured when the cavity is illuminated by a light source.

In accordance with another embodiment of the present invention, an apparatus for measuring a scattering coefficient includes a transparent material that holds an absorptive material, a diffusive material that substantially surrounds the transparent material, and light detectors that detect a diffused light intensity in the diffusive material. A light source illuminates the absorptive material with a collimated beam. A scattering coefficient for the absorptive material may be determined based on the incident light intensity of the collimated beam and the diffused light intensity measured by the light detectors when the absorptive material is illuminated.

Important technical advantages of certain embodiments of the present invention include direct measurements of absorption and scattering coefficients. As noted above, previous techniques often require indirect measurements of absorption and scattering coefficients, such as by measurement of the extinction coefficient, that can introduce errors in real-world situations. Other such techniques involve volume integration of scattered light, which requires mathematical assumptions that may not apply perfectly to real-world situations. In contrast with such methods, certain embodiments of the present invention provide direct measurement of the scattered light intensity.

Other important technical advantages of certain embodiments of the present invention include the use of open-ended detectors. Previous detectors required enclosed containers in order to accurately account for all of the light incident on the sample, because of the need for enclosure, introducing samples into the detector proved difficult, often requiring liquid samples to be pumped in and out of the detector. In contrast with such methods, certain embodiments of the present invention may accurately measure absorption and scattering coefficients even when the detector is open-ended, thus allowing the sample to be introduced into the container with relative ease compared to previous methods.

Still other technical advantages of certain embodiments of the present invention include durability under real-world use conditions. Previous enclosed detectors often included highly reflective surfaces that were prone to damage, which resulted in inaccurate measurements. Certain embodiments of the present invention protect optically sensitive components likely to be damaged by exposure to samples, thus providing a more durable detector for in situ use.

Other technical advantages of the present invention will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

For a more complete understanding of the present invention and its advantages, reference is now made to the following description, taken in conjunction with the accompanying drawings, in which:

FIG. 2 is a perspective view from one end of the detector of FIG. 1;

FIG. 3 is a flow chart illustrating one example of a method for measuring an absorption coefficient; and FIG. 4 is a flow chart illustrating one example of a method for measuring a scattering coefficient.

DETAILED DESCRIPTION OF EXAMPLE EMBODIMENTS OF THE INVENTION

Figure 1:
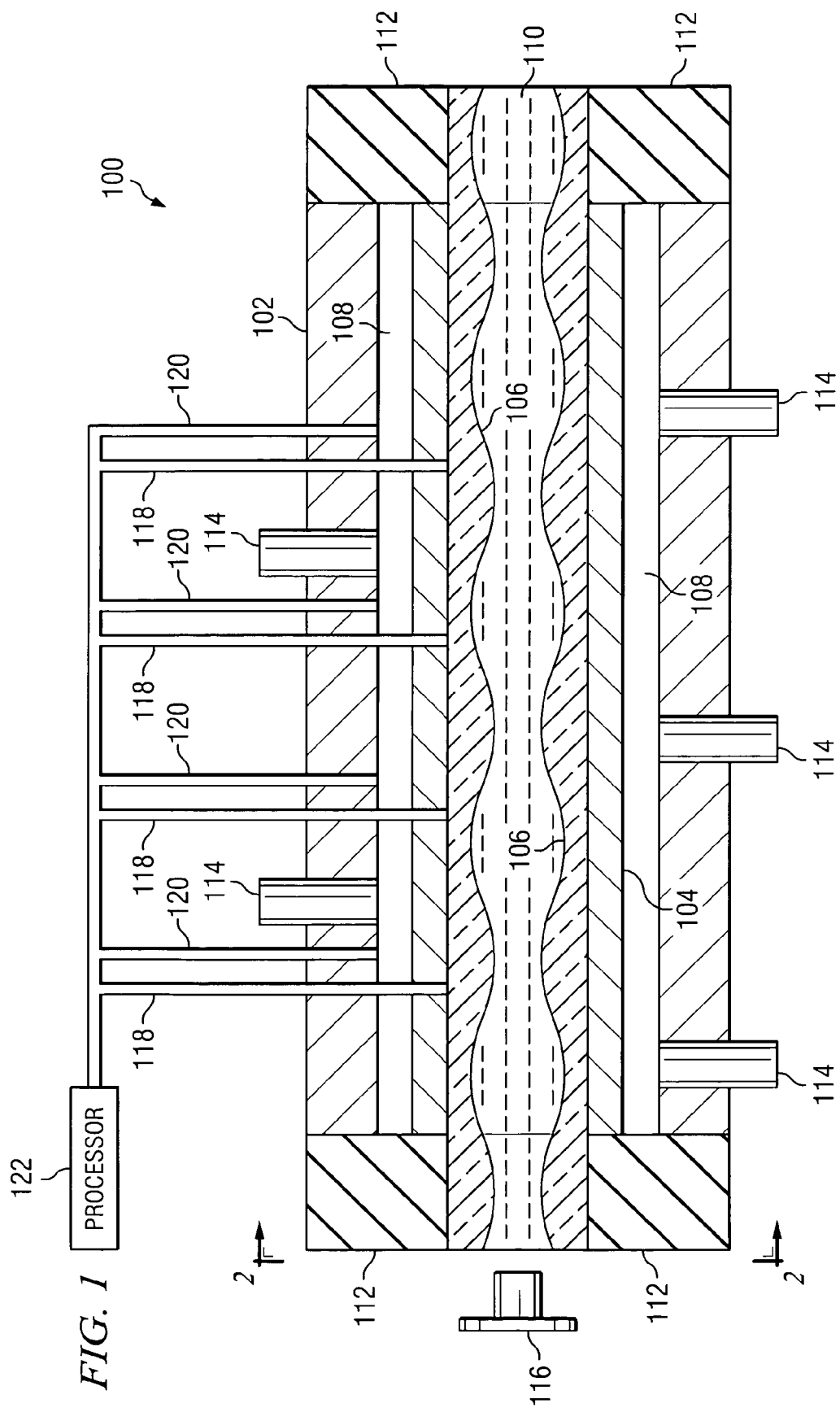
FIG. 1 is a rectangular cross-section of a cylindrical detector according to a particular embodiment of the present invention.

FIG. 1 shows a rectangular cross section of a cylindrical detector 100 used for detecting absorption and/or scattering coefficients for an absorptive material 110 within detector 100, and FIG. 2 illustrates a perspective view from the end of detector 100 taken along lines 2-2 of FIG. 1. In the depicted embodiment, detector 100 includes an outer diffusive material 102, an inner diffusive material 104, a transparent material 106 between absorptive material 110 and inner diffusive material 104, light sources 114 and 116 for introducing light into detector 100, and detectors 118 and 120 used to measure light intensity levels at different locations in detector 100. In general, detector 100 permits the direct measurement of absorption and scattering coefficients for absorptive material 110.

Outer diffusive material 102 and inner diffusive material 104 comprise materials that diffuse incoming light such that the light in the medium of diffusive materials 102 and 104 is approximately isotropic. Thus, scattered photons or other light energy in diffusive materials 102 and 104 contributes to the overall intensity of light in diffusive materials 102 and 104, but does not produce local variations in light intensity. This allows a measurement of the overall intensity of light in inner diffusive material 102 and outer diffusive material 104 without regard to positioning sensors in order to capture particular light rays. In particular embodiments in which detector 100 is substantially cylindrical, it is desirable for detector 100 to be significantly longer than its diameter in order to minimize leakage from the ends, thus increasing the accuracy of detector 100. In a particular embodiment, outer diffusive material 102 and inner diffusive material 104 may be formed from highly diffusive materials having high reflectance, such as those manufactured by SPECTRALON, which are known in the art as "Spectralon cavities."

Transparent material 106 forms a tube within detector 100 that separates absorptive material 110 from inner diffusive material 104. Transparent tube 106 should be substantially transparent to the wavelength of interest being measured for absorptive and scattering properties. Transparent tube 106 is in contact with diffusive material 104 allowing light to leak from inner diffusive material 104 to absorptive material 110 and vice versa. This protects the surface of inner diffusive material 104 from contact with absorptive material 110, which may increase its durability and protect inner diffusive surface 104 from damage resulting from contact with absorptive medium 110. In the depicted embodiment, transparent material 106 has a wavy inner surface that follows a generally sinusoidal curvature. The purpose for this feature will be described in greater detail below.

Cavity 108 between outer diffusive material 102 and inner diffusive material 104 provides a space for introduction of light into detector 100. Because cavity 108 is separated from absorptive material 110 by inner diffusive material 104, light introduced into cavity 108 will reach absorptive material 110 in a nearly isotropic manner. Accordingly, the directional effects for absorption in absorptive material 110 are diminished by the isotropy of the illumination of absorptive material 110. Furthermore, the separation between outside diffusive material 102 and inside diffusive material 104 created by cavity 108 permits measurement of light intensity both as introduced into detector 100 measured in outer diffusive material 102, and after absorption by absorptive material 110, measured in inner diffusive material 104. Cavity 108 may in principle be filled with any transparent material including air.

Absorptive material 110 represents any suitable substance to be studied that absorbs and/or scatters light. Substances of interest may include water with suspended particles, plastics, tissues, fluids, or any other substance to be characterized by absorptive or scattering properties. In a particular embodiment, detector 100 may be used to study ocean water 110 in real world settings, such as oceanographic vessels.

Light sources 114 represent any suitable source of illumination for cavity 108 in order to allow measure of absorption coefficients. In a particular embodiment, light sources 114 may be optical fibers coupled to light sources that deliver light from the sources to cavity 108. However, light sources 114 may include wave guides, phosphorescent materials, filaments, or other suitable sources of illumination. Depending on the nature of light sources 114, light sources 114 may be isolated from outer diffusive region 102 by a suitable coating or other barrier between light sources 114 and diffusive material 102, so that light from light source 114 does not increase the light intensity in outer diffusive material 102 other than by leakage from cavity 108. This prevents photons from light source 114 that may have directional properties from interfering with the isotropy of light in outer diffusive material 102.

Light source 116 introduces light into absorptive material 110 to measure scattering from absorptive material 110. It is desirable for light emitted from light source 116 to be well collimated so that the energy from light source 116 is effectively delivered into absorptive material 110. This allows the determination of the amount of scattered light to be assessed accurately based on the intensity of incoming light from light source 116. The curved inner surface of transparent material 106 facilitates scattering measurements by increasing the probability that light scattered at small angles will not be returned into absorptive material 110 by specular reflection and travel outside of the end of detector 100. For similar reasons, it is desirable that the light from light source 116 not impinge directly on the surface of transparent material 106.

Light detectors 118 and 120 may include any suitable device for measuring intensity of light at a desired wavelength. In a particular embodiment, light detectors 118 and 120 are optical fibers that carry light from outer diffusive material 102 and inner diffusive material 104 to photodetectors that measure light intensity. Photodetectors may include photodiodes, photomultipliers, photoelectric detectors or any other suitable form of light detection. In order to increase the accuracy of light intensity determination, it may be desirable to isolate light detectors 118 and 120 from particular regions of detector 100. For example, light detector 118 may be encased in an opaque covering such as aluminum foil in the region of outer diffusive material 102 and cavity 108 so that the measurement of light intensity is solely in inner diffusive material 104.

Processor 122 comprises any suitable hardware of software for processing information. In particular, processor 122 includes electronic or other types of components for receiving information from light detectors 118 and 120 and calculating absorption and scattering coefficients based on that information. Processor 122 may include components for information storage (such as magnetic memory), input devices for receiving information from detectors and/or users, output devices for displaying or otherwise generating an output of results, and any other appropriate component useful for performing tasks related to the measurement of absorption and scattering coefficients.

End caps 112 hold the components of detector 100 in a fixed arrangement. End caps 112 may be ring shaped and may be composed of any suitable material that can be affixed to outer diffusive material 102 and inner diffusive material 104. End caps 112 may also secure transparent material 106 in place as well. End caps 112 may also form part of a housing (not shown), which may be an integral piece or formed from several pieces. Such a housing may encase the components of detector 100 to protect them from exposure to the elements and other hazards and potentially damaging influences in the environment.

In general, detector 100 should be sized so as to allow adequate optical separation between inner diffusive material 102 and outer diffusive material 104, typically several millimeters. Furthermore, the length of detector 100 along its longitudinal axis (the direction of lines 2-2 in FIG. 1) should be significantly longer than the transverse dimension of the sample space holding absorptive material 110 in order to avoid light leakage. As an example, for a cylindrical, meter-long detector 100, the inner diameter of transparent material 106 could be around ten millimeters.

In operation, detector 100 may function in one of two modes. In the first mode, detector 100 measures the absorption coefficient of absorptive material 110. In the second mode of operation, detector 100 measures the scattering coefficient of absorptive material 110.

For the first mode of operation, detector 100 is filled with absorptive material 110. Light is introduced into cavity 108 by light sources 114. Once equilibrium light state is achieved in detector 100, the light intensity levels are measured in outer diffusive material 102 and inner diffusive material 104 by light detectors 120 and 118, respectively. Based on these measurements the absorption coefficient of absorptive material 110 may be determined.

In the second mode of operation, light is introduced into detector 100 by light source 116. Light is scattered by absorptive material 110, passing through transparent material 106 to diffusive material 104. Diffusive material 104 diffuses scattered light so that the intensity of light in diffusive material 104 represents the intensity of light scattered by absorptive material 110. This intensity is measured by light detectors 118, and the scattering coefficient may then appropriately determined based on the amount of light introduced into detector by light source 116. Note that the measurement of light intensity in outer diffusive region 102 is not necessary to determine the scattering intensity. Accordingly, for a detector 100 that is used to measure only scattering coefficients, detector 100 may omit outer diffusive region 102, light sources 114, and detectors 120. In such a case, inner diffusive material 104 may be encased in a reflective material to prevent light from escaping or being absorbed.

The absorption and scattering coefficients may be determined by modeling the properties of detector 100 based on the particular materials and construction used. One example is described for an embodiment in which diffusive materials 102 and 104 are Spectralon cavities, transparent material 106 is a quartz tube, and absorptive material 110 is ocean water. The Spectralon cavities can be modeled as an ideal Lambertian emitter and reflector, which emits equal radiance into all directions. The surface albedo of the Spectralon is taken as 0.994 as an assumption, although other values can be used. It is also reasonably assumed that the quartz tube neither absorbs nor scatters the light but does produce some specular reflection. The index of refraction of the quartz is assumed to be 1.46. The water itself has an index of refraction of 1.338. A Henyey-Greenstein phase function, given by $$p(\theta, \phi) = \frac{1}{4\pi} \frac{1-g^2}{(1-2g\cos\theta+g^2)^{\frac{3}{2}}}, g = \langle \cos\theta \rangle,$$

is used to model the directional dependence of the scattering, as this allows easy exploration of the effect of the shape of the volume scattering function on the recorded signal. The cylindrical symmetry of detector 100 means that the phase function is independent of azimuthal angle $\phi$. The g-parameter is equal to the average cosine of the scattering angle $\theta$. The g=0 case represents isotropic scattering. The g=0.97 case is chosen to represent a "characteristic upper limit" for real ocean water, in this case most of the scattered light travels forward. For an absolute upper limit the value g=0.99 is chosen, in that this case can be considered as one in which almost all the scattered light travels forward. For most applications with ocean water, the calculation is not particularly sensitive to variation in g-values within an ordinary range, and accordingly, this variation can be ignored, although the calibration curve may include variation for g-values as well if desired. The described relationships can be exploited to determine calibration curves for detectors 118 and 120, which in turn allow subsequent measurements of scattering coefficients using detectors 118 and 120.

FIG. 2 illustrates a perspective view from the end of detector 100 taken along lines 2—2 in FIG. 1. From this perspective, the ring shape of end cap 112 is clearly visible. The inside structure of detector 100 is shown by dashed lines, which illustrate cavity 108 separating outer diffusive material 102 and inner diffusive material 104. Transparent material 106 extends out from the inner surface of inner diffusive material 104 so that transparent material 106 is visible looking through the hole at the end of detector 100. Within the space enclosed by transparent material 106 is absorptive material 110. As depicted on the sides, light sources 114 and detectors 118 and 120 (hidden from this perspective by detector 118) extend into the sides of detector 100.

Although particular embodiments of detector 100 have been described in detail, it should be understood that these embodiments are only examples, and that numerous modifications and variations of the basic principles are possible. For example, as discussed above, detector 100 may be enclosed in a variety of housings, and may be assembled in any suitable manner. If detector 100 does not need to be used in measuring absorption coefficient, outer diffusive medium 102 and associated components may be left out of detector 100. In the opposite case, in which scattering is not measured, specular reflection from the interface between transparent material 106 and absorptive material 110 is a much less significant concern, and accordingly, the inner surface of transparent material 106 may be made smooth. Other physical configurations of detector 100 may also be used in different geometrical symmetries may be designed, although other geometries may require more complicated placements of detectors 118 and 120 and the calculations performed based on resulting measurements. These and other variations should be understood to be encompassed within the embodiments described above.

FIG. 3 is a flow chart 200 illustrating a method for measuring an absorption coefficient of an absorptive material 110. The first three steps of the illustrated method are calibration steps to determine the proper settings for detectors 118 and 120, in which detector 100 may be filled with a reference material having known optical properties. Cavity 108 is illuminated at step 202. At step 204, light intensity is measured in inner diffusive material 104 and outer diffusive material 102. Detectors 118 and 120 are calibrated according to the known absorptive value at step 206. This step may also involve adjusting the light intensity to determine whether the scaling of the results is appropriate to enable determination of the accuracy of detectors 118 and 120.

To measure the absorptive qualities of absorptive material 110, absorptive material 110 is inserted into detector 100 at step 208. Cavity 108 is illuminated using light sources 114 at step 210. Light intensities are measured in diffusive regions 102 and 104 using detectors 118 and 120 at step 212. Based on the previous calibration, and the results of the measurement, absorptive coefficient is determined at step 214.

FIG. 4 is a flowchart 220 that illustrates an example of a method for measuring scattering coefficient. The first three steps of the illustrated method are calibration steps, in which detector 100 may be filled with a reference material with known optical properties. The inside of the tube formed by transparent material 106 is illuminated at step 222 while detector 100 is filled with a reference material. The light intensity in the inner and outer diffusive materials 102 and 104 is measured at step 224. During this step the light intensity produced by light source 116 may be adjusted to ensure that the proper relationship between intensity and scattering coefficient is being observed by detectors 118 and 120. Based on those measurements, detectors are calibrated at step 226.

To measure scattering coefficient, a light-scattering material is introduced into detector at step 228. The light-scattering material 110 is illuminated using light source 116 at step 230. Light intensity in inner diffusive material 104 is measured using detectors 118 at step 232. The incoming light intensity from light source 116 is determined at step 234. This light intensity may be known from the properties of light source 116, or may be measured using photo detectors or other suitable techniques. Based on the measured light intensity in diffusive material 104 and the light intensity incident on light scattering material 110, the scattering coefficient may be determined.

Although the present invention has been described with several embodiments, a myriad of changes, variations, alterations, transformations, and modifications may be suggested to one skilled in the art, and it is intended that the present invention encompass such changes, variations, alterations, transformations, and modifications as fall within the scope of the appended claims.

What is claimed is:

1. An apparatus, comprising:
   a first diffusive material having a generally cylindrical shape with a length greater than twice its diameter;
   a second diffusive material inside the first diffusive material separated from the first diffusive material by a cavity;
   a transparent material proximate an inner surface of the second diffusive material operable to hold an absorptive material, the transparent material having an inner surface that is curved along its length in a substantially sinusoidal pattern;
   first light detectors, comprising:
      first optical fibers operable to carry light from the first diffusive material; and
      first photodetectors operable to measure a first light intensity for the light carried from the first diffusive material;
   second light detectors, comprising:
      second optical fibers operable to carry light from the second diffusive material; and
      second photodetectors operable to measure a second light intensity for the light carried from the second diffusive material;
   first light sources operable to illuminate the cavity;
   a second light source operable to illuminate the absorptive material with a collimated beam having an incident light intensity; and
   a processor operable to:
      determine an absorption coefficient for the absorptive material based on a first diffused light intensity measured by the first light detectors in the first diffusive material and a second diffused light intensity measured by the second light detectors in the second diffusive material, wherein the first and second diffused light intensities are measured while the cavity is illuminated by the first light sources; and
      determine a scattering coefficient for the absorptive material based on a third diffused light intensity measured by the second light detectors in the second diffusive medium, wherein the third light intensity is measured while the absorptive material is illuminated by the collimated beam from the second light source.

2. A method for measuring an absorption coefficient, comprising:
   introducing light into a cavity between a first diffusive material and a second diffusive material, wherein at least some of the light in the cavity passes into the first and second diffusive material and at least some of the light passing into the second diffusive material passes through a transparent material proximate to the second diffusive material and into an absorptive material;
   measuring a first intensity comprising the intensity of the light in the first diffusive material;
   measuring a second intensity comprising the intensity of the light in the second diffusive material; and
   determining an absorption coefficient for the absorptive material based on the first and second intensity measurements.

3. The method of claim 2, wherein the first and second diffusive materials are Spectralon cavities.

4. The method of claim 2, wherein the first and second diffusive materials comprise concentric cylindrical shells; and the cavity comprises a cylindrical space between the first and second diffusive materials.

5. The method of claim 2, wherein the transparent material comprises a quartz tube.

6. The method of claim 2, wherein the transparent material comprises an inner surface that is curved along the length of the transparent material.

7. The method of claim 6, wherein the curvature of the inner surface is substantially sinusoidal.

8. The method of claim 2, further comprising:
stopping the introduction of light into the cavity;
after stopping the introduction of light into the cavity, illuminating the absorptive material using a collimated beam, wherein scattered light from the absorptive material passes through the transparent material to the second diffusive material and light is not introduced into the cavity while the collimated beam is illuminating the absorptive material;
after illuminating the absorptive material with the collimated beam, measuring a new value of the second light intensity in the second diffusive material;
determining an incident light intensity for the collimated beam; and
determining a scattering coefficient of the absorptive material based on the incident light intensity and the new value of the second light intensity.

9. An apparatus, comprising:
a first diffusive material;
a second diffusive material inside the first diffusive material separated from the first diffusive material by a cavity;
a transparent material proximate to an inner surface of the second diffusive material operable to hold an absorptive material;
first light detectors operable to measure a first light intensity in the first diffusive material; and
second light detectors operable to measure a second light intensity in the second diffusive material, wherein an absorption coefficient for the absorptive material in the transparent material may be determined based on the first and second light intensities measured when the cavity is illuminated by a light source.

10. The apparatus of claim 9, further comprising a processor operable to determine the absorption coefficient of the absorptive materials based on the first and second light intensities.

11. The apparatus of claim 9, wherein the first and second diffusive materials are Spectralon cavities.

12. The apparatus of claim 9, first and second diffusive materials comprise concentric cylindrical shells; and the cavity comprises a cylindrical space between the first and second diffusive materials.

13. The apparatus of claim 9, wherein the transparent material comprises a quartz tube.

14. The apparatus of claim 9, wherein the transparent material comprises an inner surface that is curved.

15. The apparatus of claim 14, wherein the curvation of the inner surface is substantially sinusoidal.

16. The apparatus of claim 9, further comprising an additional light source operable to illuminate the absorptive material with a collimated beam having an incident light intensity, wherein a scattering coefficient may be determined based on the second light intensity then the absorptive material is illuminated by the collimated beam and the incident light intensity.

17. A method for measuring a scattering coefficient, comprising:
illuminating an absorptive material with a collimated beam having an incident light intensity, wherein the absorptive material is within a transparent material substantially surrounded by a diffusive material;
measuring a diffused light intensity in the diffusive material; and
determining a scattering coefficient for the absorptive material based on diffused light intensity and the incident light intensity.

18. The method of claim 17, wherein the diffusive material is a Spectralon cavity.

19. The method of claim 17, wherein the diffusive material comprises a cylindrical shell.

20. The method of claim 17, wherein the transparent material comprises a quartz tube.

21. The method of claim 17, wherein the diffusive material is enclosed by a reflective material having a reflective inner surface.

22. The method of claim 17, wherein the diffusive material is a first diffusive material, and the first diffusive material is substantially surrounded by a second diffusive material separated from the first diffusive material by a cavity.

23. The method of claim 22, further comprising:
illuminating the cavity;
measuring a first diffused light intensity in the first diffusive material;
measuring a second diffused light intensity in the second diffusive material; and
determining an absorption coefficient for the absorptive material based on the first and second diffused light intensities.

24. An apparatus, comprising:
a transparent material operable to hold an absorptive material;
a diffusive material substantially surrounding the transparent material;
light detectors operable to detect a diffused light intensity in the diffusive material;
a light source operable to illuminate an absorptive material with a collimated beam having an incident light intensity, wherein a scattering coefficient for the absorptive material may be determined based on the incident light intensity and the diffused light intensity.

25. The apparatus of claim 24, further comprising a processor operable to determine the scattering coefficient for the absorptive material based on the incident light intensity and the diffused light intensity.

26. The apparatus of claim 24, wherein the diffusive material is a Spectralon cavity.

27. The apparatus of claim 24, wherein the diffusive material comprises a cylindrical shell.

28. The apparatus of claim 24, wherein the transparent material comprises a quartz tube.

29. The apparatus of claim 24, wherein the diffusive material is enclosed by a reflective material having a reflective inner surface.

30. The apparatus of claim 24, wherein the diffusive material is a first diffusive material, and the first diffusive material is substantially surrounded by a second diffusive material separated from the first diffusive material by a cavity.

31. The apparatus of claim 30, wherein:
the light source is a first light source, the light detectors are first light detectors, and the diffused light intensity is a first diffused light intensity;
the apparatus further comprises:
a second light source operable to illuminate the cavity;
second light detectors operable to measure a second diffused light intensity in the second diffusive material; and
an absorption coefficient for the absorptive material may be determined based on the first and second diffused light intensities when the cavity is illuminated.

* * * * *